United States Patent
Rault et al.

(10) Patent No.: US 7,361,662 B2
(45) Date of Patent: Apr. 22, 2008

(54) PYRIDOPYRIMIDINONE COMPOUNDS, METHOD FOR PRODUCTION THEREOF AND MEDICAMENTS COMPRISING THE SAME

(75) Inventors: Sylvain Rault, Moult (FR); Jean-Charles Lancelot, Le Bourg (FR); Marina Kopp, Caen (FR); Daniel-Henri Caignard, Le Pecq (FR); Bruno Pfeiffer, Saint Leu la Foret (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 108 days.

(21) Appl. No.: 10/533,697

(22) PCT Filed: Nov. 4, 2003

(86) PCT No.: PCT/FR03/03274

§ 371 (c)(1), (2), (4) Date: May 3, 2005

(87) PCT Pub. No.: WO2004/043956

PCT Pub. Date: May 27, 2004

(65) Prior Publication Data

US 2005/0288311 A1 Dec. 29, 2005

(30) Foreign Application Priority Data

Nov. 5, 2002 (FR) .................................. 02 13804

(51) Int. Cl.
- C07D 471/04 (2006.01)
- C07D 295/12 (2006.01)
- A61K 31/519 (2006.01)
- A61P 3/06 (2006.01)

(52) U.S. Cl. .............................. 514/264.11; 514/228.5; 514/234.5; 514/234.2; 514/217.06; 544/61; 544/117; 544/279

(58) Field of Classification Search ........... 514/264.11, 514/228.5, 234.5, 217.06, 234.2; 544/279, 544/61, 117; 540/600
See application file for complete search history.

(56) References Cited

U.S. PATENT DOCUMENTS

| | | | |
|---|---|---|---|
| 6,060,477 A | 5/2000 | Rafat et al. | |
| 6,066,462 A * | 5/2000 | Goueli | 435/7.1 |
| 6,313,292 B1 | 11/2001 | William et al. | |
| 6,962,922 B2 * | 11/2005 | Gaudilliere et al. | 514/266.2 |
| 2005/0080096 A1 * | 4/2005 | Ishida et al. | 514/260.1 |

FOREIGN PATENT DOCUMENTS

| WO | WO 9802438 | 1/1998 |
|---|---|---|
| WO | WO 9805661 | 2/1998 |

OTHER PUBLICATIONS

Gilbert, et al., Does protein kinase R mediate TNF-alpha and ceramide-induced increases in expression and activation of matrix metalloproteinases in articular cartilage by a novel mechanism?, Arthritis Research & Therapy, vol. 6, No. 1, pp. R46-R55, Nov. 12, 2003.*
Rask-Madsen, et al., Proatherosclerotic Mechanisms Involving Protein Kinase C in Diabetes and Insulin Resistance, Arterioscler. Throm. Basc. Biol., Mar. 2005, pp. 487-496.*
Leng, et al., WNK3, a kinase related to genes mutated in hereditary hypertension with hyperkalaemia, regulates the K= channel ROMK1 (Kir1.1), J. Physiol., 2006, pp. 275-286.*
On-Line Medical dictionary, http://cancerweb.ncl.ac.uk/cgi-bin/omb?query=kinase&action=Search+OMB;http://cancerweb.ncl.ac.uk/cgi-bin/omb?query=PHOSPHOKINASE &action=Search+OMB; http://cancerweb.ncl.ac.uk/cgi-bin/omb?ENZYME; downloaded Aug. 15, 2006.*
http://www.oncolink.com/types/index.cfm, List of Cancers.*
Walsh, BBC News, International Version, Medical Notes, Feb. 1, 2007.*
PharmaLicensing (Mar. 2005).*
Serrels, et al., Mol. Cancer Ther., 2006, 5 (12), Dec. 2006.*
JH Maguire "The Synthesis of a pyrido'3,4-d!pyrimidine analog of peteroic acid" J Het. Chem. vol. 16, 1979, p. 133-136.
International Search Report: PCT FR2003 003274, Mar. 23, 2004.
Internation Preliminary Examination Report: PCT FR2003 003274, May 19, 2004.

* cited by examiner

*Primary Examiner*—Mark Berch
*Assistant Examiner*—Cecilia M Jaisle
(74) *Attorney, Agent, or Firm*—Hueschen and Sage

(57) ABSTRACT

A compound of formula (I):

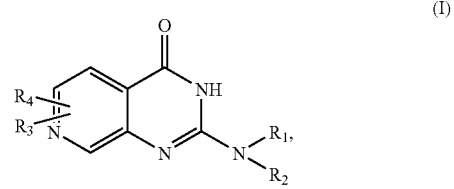

wherein:

$R_1$, $R_2$, $R_3$, $R_4$ are defined in the description, its enantiomers, diastereoisomers, tautomers and also addition salts thereof with a pharmaceutically acceptable acid or base, and medicinal products containing the same which are useful as kinase modulators.

12 Claims, No Drawings

PYRIDOPYRIMIDINONE COMPOUNDS, METHOD FOR PRODUCTION THEREOF AND MEDICAMENTS COMPRISING THE SAME

The present invention relates to new pyridopyrimidinone compounds, to a process for their preparation and to pharmaceutical compositions containing them.

The compounds of the invention are new and have valuable modulatory properties with respect to a panel of kinases, making them of use in the treatment of numerous types of disorders, amongst which there may be mentioned, without implying any limitation: cancer, arthrosis, diabetes, obesity, hypertension etc.. In addition, they are completely non-toxic. Moreover, to our knowledge, this family of compounds is completely novel and the activity that we have discovered in them has not been mentioned for structurally close compounds.

More specifically, the present invention relates to compounds of formula (I):

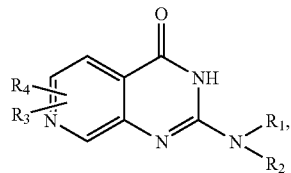

wherein:

$R_1$ and $R_2$, which are the same or different, represent a hydrogen atom or an alkyl group or together with the nitrogen atom carrying them form a heterocycle, $R_3$ represents a halogen atom, an alkoxy group, an optionally substituted aryl group or a group $NR'_1R'_2$ wherein $R'_1$ and $R'_2$, which are the same or different, represent a hydrogen atom or an alkyl group or together with the nitrogen atom carrying them form a heterocycle, $R_4$ represents a hydrogen atom or a group $NR''_1R''_2$ wherein $R''_1$ and $R''_2$, which are the same or different, represent a hydrogen atom or an alkyl group or together with the nitrogen atom carrying them form a heterocycle, to their enantiomers, diastereoisomers, tautomers and also to addition salts thereof with a pharmaceutically acceptable acid or base, it being understood that:
the term "alkyl" denotes a linear or branched hydrocarbon chain containing from 1 to 8 carbon atoms,
the term "alkoxy" denotes an alkyl-oxy group wherein the alkyl chain is linear or branched and contains from 1 to 8 carbon atoms,
the term "aryl" denotes a phenyl or naphthyl group,
the term "heterocycle" denotes a mono- or bi-cyclic system which contains from 5 to 11 carbon atoms and which may contain, in addition to the nitrogen atom to which $R_1R_2$, $R'_1R'_2$ or $R''_1R''_2$ are bonded, one or two further hetero atoms selected from oxygen, sulphur and nitrogen, it being possible for the heterocyclic system to be substituted by one, two or three alkyl groups,
the term "substituted" associated with an aryl group indicates that the phenyl or naphthyl group is substituted by one, two or three identical or different groups selected from halogen atoms and alkyl, alkoxy, polyhaloalkyl and hydroxy groups, "polyhaloalkyl" being understood to be a linear or branched carbon chain containing from 1 to 3 carbon atoms and from 1 to 7 halogen atoms.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc..

Among the pharmaceutically acceptable bases there may be mentioned, without implying any limitation, sodium hydroxide, potassium hydroxide, triethylamine etc..

An advantageous embodiment of the invention relates to compounds of formula (I'):

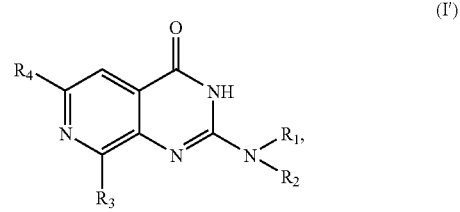

to their enantiomers, diastereoisomers, tautomers and also to addition salts thereof with a pharmaceutically acceptable acid or base.

Another advantageous embodiment of the invention relates to compounds wherein $NR_1R_2$ represents an $NH_2$ group, a di-n-propylamine group or also a morpholine group, to their enantiomers, diastereoisomers, tautomers and also to addition salts thereof with a pharmaceutically acceptable acid or base.

Preferred compounds of the invention are those wherein $R_3$ represents a 3,4-dimethoxyphenyl, 3,5-dimethylmorpholine, thiomorpholine, azepine, perhydroquinoline or pyrrolidine group or a chlorine atom, their enantiomers, diastereoisomers, tautomers and also addition salts thereof with a pharmaceutically acceptable acid or base.

Another advantageous embodiment of the invention relates to compounds wherein $R_4$ represents a hydrogen atom or a morpholine or azepine group, to their enantiomers, diastereoisomers, tautomers and also to addition salts thereof with a pharmaceutically acceptable acid or base.

Among the preferred compounds of the invention there may be mentioned:
2-(dipropylamino)-8-(4-thiomorpholinyl)pyrido[3,4-d]pyrimidin-4(3H)-one,
8-(1-azocanyl)-2-(dipropylamino)pyrido[3,4-d]pyrimidin-4(3H)-one,
8-((4aα,8aα)-octahydro-1(2H)-quinolyl)-2-(dipropylamino)pyrido[3,4-d]pyrimidin-4(3H)-one,
8-((4aβ,8aα)-octahydro-1(2H)-quinolyl)-2-(dipropylamino)pyrido[3,4-d]pyrimidin-4(3H)-one,
6,8-di(1-azepanyl)-2-(dipropylamino)pyrido[3,4-d]pyrimidin-4(3H)-one,
8-(1-azepanyl)-2-(dipropylamino)-6-(4-morpholinyl)pyrido[3,4-d]pyrimidin-4(3H)-one,
8-(1-azepanyl)-2,6-di(4-morpholinyl)pyrido[3,4-d]pyrimidin-4(3H)-one,
2-amino-8-[(3α,5β)-3,5-dimethylmorpholinyl]pyrido[3,4-d]pyrimidin-4(3H)-one,
2-amino-8-[(3α,5α)-3,5-dimethylmorpholinyl]pyrido[3,4-d]pyrimidin-4(3H)-one,
8-[(3α,5β)-3,5-dimethylmorpholinyl]-2-(dipropylamino)pyrido[3,4-d]pyrimidin-4(3H)-one, 8-[(3α,5α)-3,5-dimethylmorpholinyl]-2-(dipropylamino)pyrido[3,4-d]pyrimidin-4(3H)-one, 8-[(3α,5α)-3,5-dimethylmorpholinyl]-2-(4-morpholinyl)pyrido[3,4-d]pyrimidin-4(3H)-one, 2-amino-8-(1-azepanyl)-6-(4-morpholinyl)pyrido[3,4-d]pyrimidin-4(3H)-one, 8-chloro-2-(dipropylamino)pyrido[3,4-d]pyrimidin-4(3H)-one, 2-(dipropylamino)-8-(1-pyrrolidinyl)pyrido[3,4-d]pyrimidin-4(3H)-one, and 8-(3,4-dimethoxyphenyl)-2-(dipropylamino)pyrido[3,4-d]pyrimidin-4(3H)-one, their tautomers and addition salts thereof with a pharmaceutically acceptable acid.

The invention relates also to a process for the preparation of the compounds of formula (I), which process is characterised in that there is used as starting material a compound of formula (II):

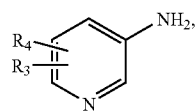

(II)

wherein:

$R_3$ and $R_4$ are as defined for formula (I), which is condensed with a compound of formula (III):

S=C=N—C(O)OR$_{20}$ (III), wherein $R_{20}$ represents an alkyl or aryl-alkyl group, to yield a compound of formula (IV):

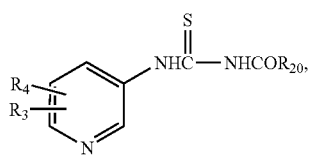

(IV)

wherein:

$R_3$, $R_4$ and $R_{20}$ are as defined hereinbefore, which compound of formula (IV) is condensed in the presence of a metallic salt with the amine (V):

HN $R_1$ $R_2$ (V),

wherein:

$R_1$ and $R_2$ are as defined for formula (I), to yield a compound of formula (I), which may be, where appropriate, purified according to a conventional purification method, which is separated, where applicable, into its stereoisomers according to a conventional separation technique, which is converted, if desired, into its addition salts with a pharmaceutically acceptable acid or base, it being understood that:

at any time considered to be appropriate in the course of the process described above, the amino or alkylamino group(s) of the starting reagent (II) may be protected and then, after condensation, deprotected for the requirements of synthesis, the reagents (II) are described in the literature or are prepared according to known procedures described in the literature.

The compounds of the invention have been studied in relation to a group of kinases, with respect to which they have shown excellent activity. This activity is generally specific to a particular type of kinase, the type varying as a function of the structure of the compound of formula (I).

Depending on the type of kinase with respect to which the compound of the invention is active, it may be expected to have excellent activity in various types of cancers, in metabolic disorders and, more especially, in the treatment or prophylaxis of hyperglycaemias, dyslipidaemias such as hypercholesterolaemia and hyperlipidaemia and also in the treatment of non-insulin-dependent, type II diabetes, obesity and complications of diabetes especially in the cardiovascular area, or also in inflammatory disorders such as arthrosis or, finally, in cardiovascular disorders not associated with diabetes such as arterial hypertension. Moreover, the fact that the compounds of the invention are completely non-toxic makes them undeniably valuable for therapeutic use.

The present invention relates also to pharmaceutical compositions comprising as active ingredient at least one compound of formula (I), alone or in combination with one or more inert, non-toxic, pharmaceutically acceptable excipients or carriers.

Among the pharmaceutical compositions according to the invention there may be mentioned more especially those that are suitable for oral, parenteral and nasal administration, tablets or dragées, sublingual tablets, gelatin capsules, lozenges, suppositories, creams, ointments and dermal gels etc..

The useful dose varies according to the age and weight of the patient, the nature and severity of the disorder and the administration route, which may be oral, nasal, rectal or parenteral. Generally, the unit dose ranges from 0.01 to 500 mg per 24 hours, for treatment in from 1 to 3 administrations.

The Examples that follow illustrate the invention, without limiting it in any way. The structures of the compounds described have been confirmed by customary spectroscopic and spectrometric techniques.

The starting materials used are known products or are prepared according to known procedures.

A (4aα,8aα) compound is understood to mean a compound wherein the relevant ring junction is of the cis configuration.

A (3α,5α) compound is understood to mean a compound wherein the relevant ring junction is of the cis configuration.

A (4aβ,8aα) compound is understood to mean a compound wherein the relevant ring junction is of the trans configuration.

A (3α,5β) compound is understood to mean a compound wherein the relevant ring junction is of the trans configuration.

EXAMPLE 1

8-(1-Azocanyl)-2-(dipropylamino)pyrido[3,4-d]pyrimidin-4(3H)-one

A mixture of 0.02 mol (4.10 g) of 3-amino-2-azocanopyridine and 0.02 mol of ethoxy-carbonyl isothiocyanate is stirred at ambient temperature for 3 hours in 100 ml of DMF, by which means the thiourea of formula (IV) is obtained, which it is not necessary to isolate. The solution is cooled to 0° C. and saturated with 2.5 eq. of di-n-propylamine, and 0.02 mol of mercuric chloride is added; at the end of 15 minutes, the ice bath is removed and the mixture is stirred at ambient temperature for 3 hours (the black precipitate caused by the formation of mercury sulphide will still be seen to appear). After having added 150 ml of ethyl acetate, the solution is filtered over Celite and the solvents are evaporated off under reduced pressure. The crude N-ethoxycarbonylguanidine thereby obtained is again dissolved in 50 ml of DMF and heated at reflux for 2 hours. After the hot solution has been filtered in order to remove the last remnants of mercury salt, the DMF is evaporated off under reduced pressure. The solid thereby obtained is taken up in a minimum of acetonitrile, filtered off over a frit under suction and then recrystallised from acetonitrile.

Melting point: 172° C.

EXAMPLE 2

8-(4-Thiomorpholinyl)-2-(dipropylamino)pyrido[3,4-d]pyrimidin-4(3H)-one

By proceeding as in Example 1, but replacing the 3-amino-2-azocanopyridine by 3-amino-2-(4-thiomorpholinyl)pyridine, the title compound is obtained.

Melting point: 226° C.

EXAMPLE 3

8-((4aα,8aα)-Octahydro-1(2H)-quinolyl)-2-(dipropylamino)pyrido[3,4-d]pyrimidin-4(3H)-one By proceeding as in Example 1, but replacing the 3-amino-2-azocanopyridine by 2-((4aα,8aα)-octahydro-1(2H)-quinolyl)-3-pyridinamine, the title compound is obtained.

Melting point: 215° C.

EXAMPLE 4

8-((4aβ,8aα)-Octahydro-1(2H)-quinolyl)-2-(dipropylamino)pyrido[3,4-d]pyrimidin-4(3H)-one By proceeding as in Example 1, but replacing the 3-amino-2-azocanopyridine by 2-((4aβ,8aα)-octahydro-1(2H)-quinolyl)-3-pyridinamine, the title compound is obtained.

Melting point: 225° C.

EXAMPLE 5

6,8-Di(1-azepanyl)-2-(dipropylamino)pyrido[3,4-d]pyrimidin-4(3H)-one

By proceeding as in Example 1, but replacing the 3-amino-2-azocanopyridine by 3-amino-2,6-diazepanopyridine, the title compound is obtained.

Melting point: 220° C.

EXAMPLE 6

8-(1-Azepanyl)-2-(dipropylamino)-6-(4-morpholinyl)pyrido[3,4-d]pyrimidin-4(3H)-one By proceeding as in Example 1, but replacing the 3-amino-2-azocanopyridine by 3-amino-2-azepano-6-(4-morpholinyl)pyridine, the title compound is obtained.

Melting point: 250° C.

EXAMPLE 7

8-(1-Azepanyl)-2,6-di(4-morpholinyl)pyrido[3,4-d]pyrimidin-4(3H)-one

By proceeding as in Example 6 but replacing the di-n-propylamine by morpholine, the title compound is obtained.

Melting point: 240° C.

EXAMPLE 8

2-Amino-8-[(3α,5β)-3,5-dimethylmorpholinyl]pyrido[3,4-d]pyrimidin-4(3H)-one

Step A: N-ethoxycarbonyl-N'-2-(3,5-dimethymorpholin-4-yl)pyridine

A mixture of 0.02 mol of cis-/trans-3-amino-2-[4-(3,5-dimethyl)morpholinyl]pyridine (3.80 g) and 2.62 g (0.02 mol) of ethoxycarbonyl isothiocyanate is stirred at ambient temperature for 3 hours in 100 ml of DMF. The mixture obtained is poured into 200 ml of water. The precipitate that forms is filtered off under suction and washed with petroleum ether. The cis and trans isomers are separated by column chromatography (eluant: ether/cyclohexane 55/45).

Step B: 2-Amino-8-[(3α,5β)-3,5-dimethylmorpholinyl]pyrido[3,4-d]pyrimidin-4(3H)-one 0.002 mol of the cis thiourea obtained in Step A is dissolved in 100 ml of DMF and the solution thereby formed is cooled to 0° C. and then saturated with gaseous ammonia. 0.002 mol (0.50 g) of mercuric chloride is added. At the end of fifteen minutes, the ice bath is removed and the mixture is stirred at ambient temperature for 3 hours. After adding 150 ml of ethyl acetate, the solution is filtered over Celite and the solvents are evaporated off under reduced pressure. The precipitate thereby obtained is again dissolved in 50 ml of DMF and heated at reflux for two hours. After filtering whilst hot, the DMF is evaporated off under reduced pressure. The solid thereby obtained is taken up in a minimum of acetonitrile, filtered off over a frit under suction and recrystallised from acetonitrile.

Melting point: above 260° C.

EXAMPLE 9

2-Amino-8-[(3α,5α)-3,5-dimethylmorpholinyl]pyrido[3,4-d]pyrimidin-4(3H)-one

By using the trans-N-ethoxycarbonyl-N'-2-[3-(3,5-dimethyl)morpholin-4-yl)-pyridyl-thiourea obtained in Step A of Example 8 and by proceeding as in Example 8 Step B, the title compound is obtained.

EXAMPLE 10

8-[(3α,5α)-3,5-Dimethylmorpholinyl]-2-(dipropylamino)pyrido[3,4-d]pyrimidin-4(3H)-one By proceeding as in Example 8 Step B, but replacing the gaseous ammonia by 0.002 mol of di-n-propylamine, the title compound is obtained.

Melting point: 195° C.

EXAMPLE 11

8-[(3α,5β)-3,5-Dimethylmorpholinyl]-2-(dipropylamino)pyrido[3,4-d]pyrimidin-4(3H)-one By proceeding as in Example 9 and replacing the gaseous ammonia by 0.002 mol of di-n-propylamine, the title compound is obtained.

Melting point: 173° C.

EXAMPLE 12

8-[(3α,5α)-3,5-Dimethylmorpholinyl]-2-(4-morpholinyl)pyrido[3,4-d]pyrimidin-4(3H)-one By proceeding as in Example 8 Step B, but replacing the gaseous ammonia by 0.002 mol of morpholine, the title compound is obtained.

Melting point: 275° C.

EXAMPLE 13

2-Amino-8-(1-azepanyl)-6-(4-morpholinyl)pyrido[3,4-d]pyrimidin-4(3H)-one

By proceeding as in Example 6, but replacing the di-n-propylamine by gaseous ammonia, the title compound is obtained.

Sublimation at 260° C.

EXAMPLE 14

8-Chloro-2-(dipropylamino)pyrido[3,4-d]pyrimidin-4(3H)-one

By proceeding as in Example 1 and replacing the 3-amino-2-azocanopyridine by 3-amino-2-chloropyridine, the title compound is obtained.

Melting point: 180° C.

EXAMPLE 15

2-(Dipropylamino)-8-(1-pyrrolidinyl)pyrido[3,4-d]pyrimidin-4(3H)-one

By proceeding as in Example 1 and replacing the 3-amino-2-azocanopyridine by 3-amino-2-(1-pyrrolidinyl)pyridine, the title compound is obtained.

Melting point: 220° C.

EXAMPLE 16

8-(3,4-Dimethoxyphenyl)-2-(dipropylamino)pyrido[3,4-d]pyrimidin-4(3H)-one

By proceeding as in Example 1 and replacing the 3-amino-2-azocanopyridine by 3-amino-2-(3,4-dimethoxyphenyl)pyridine, the title compound is obtained.

Melting point: 202° C.

Pharmacological Study

EXAMPLE A

Screening of a Panel of Kinases

Using conventional screening methods employing commercially available kinases, the products of the invention exhibited valuable properties:
- activating properties with respect to certain kinases, for a number of products of the invention;
- inhibitory properties with respect to other kinases, for a number of products of the invention;
- potentiating properties with respect to kinase activators or inhibitors, for other products.

EXAMPLE B

Hypolipaemic Activity

The products of the invention were tested in vivo in the obese ob/ob mouse, used as a model of obesity-associated insulin resistance. By way of example, the compound of Example 6 significantly reduces the triglycerides at 125 mg/kg per os whereas, with metformin, the same reduction is obtained at 250 mg/kg per os. In this model, the compounds of the invention have thus been shown to be powerful hypolipaemic agents.

EXAMPLE C

Acute Toxicity Study

Acute toxicity was evaluated after oral administration of increasing doses of the test compound to groups each comprising 8 mice (26±6 grams). The animals were observed at regular intervals over the course of the first day and daily for the two weeks following treatment.

It appears that the compounds of the invention are completely non-toxic.

EXAMPLE D

Pharmaceutical Composition

Formulation for the preparation of 1000 tablets each containing 5 mg of active ingredient

| | |
|---|---|
| Compound of Example 8 | 5 g |
| Hydroxypropylcellulose | 2 g |
| Wheat starch | 10 g |
| Lactose | 100 g |
| Magnesium stearate | 3 g |
| Talc | 3 g |

The invention claimed is:

1. A compound of formula (I),

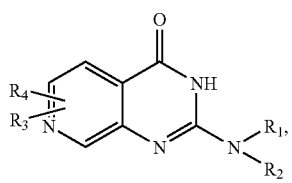

wherein:
$R_1$ and $R_2$, which are the same or different, represent hydrogen or alkyl or together with nitrogen carrying them form a heterocycle, $R_3$ represents halogen, alkoxy, an optionally substituted aryl group or $NR'_1R'_2$ wherein $R'_1$ and $R'_2$, which are the same or different, represent hydrogen or alkyl or together with nitrogen carrying them form a heterocycle, $R_4$ represents hydrogen or $NR''_1R''_2$ wherein $R''_1$ and $R''_2$, which are the same or different, represent hydrogen or alkyl or together with nitrogen carrying them form a heterocycle, its enantiomers, diastereoisomers, tautomers and addition salts thereof with a pharmaceutically acceptable acid or base, it being understood that:

the term "alkyl" denotes linear or branched hydrocarbon chain having from 1 to 8 carbon atoms, the term "alkoxy" denotes alkyl-oxy wherein the alkyl chain is linear or branched and has from 1 to 8 carbon atoms, the term "aryl" denotes phenyl or naphthyl, the term "heterocycle" denotes a mono- or bi-cyclic system which has from 5 to 11 carbon atoms and which may contain, in addition to the nitrogen atom to which $R_1R_2$, $R'_1R'_2$ or $R''_1R''_2$ are bonded, one or two further hetero atoms selected from oxygen, sulphur and nitrogen, it being possible for the heterocyclic system to be substituted by one, two or three alkyl groups, the term "substituted" associated with aryl indicates that the phenyl or naphthyl group is substituted by one, two or three identical or different groups selected from halogen, alkyl, alkoxy, polyhaloalkyl and hydroxy, "polyhaloalkyl" denotes a linear or branched carbon chain having from 1 to 3 carbon atoms and from 1 to 7 halogen atoms.

2. A compound of claim 1, which is represented by formula (I'),

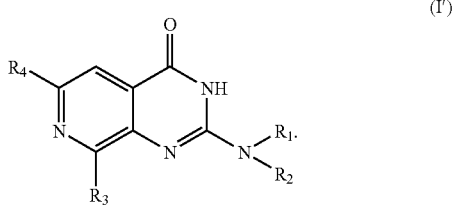

3. A compound of claim 1, wherein $NR_1R_2$ represents $NH_2$, di-n-propylamine or morpholine.

4. A compound of claim 2, wherein $NR_1R_2$ represents $NH_2$, di-n-propylamine or morpholine.

5. A compound of claim 1, wherein $R_3$ represents 3,4-dimethoxyphenyl, 3,5-dimethylmorpholine, thiomorpholine, azepine, perhydroquinoline, pyrrolidine or chlorine.

6. A compound of claim 2, wherein $R_3$ represents 3,4-dimethoxyphenyl, 3,5-dimethylmorpholine, thiomorpholine, azepine, perhydroquinoline, pyrrolidine or chlorine.

7. A compound of claim 1, wherein $R_4$ represents hydrogen, morpholine or azepine.

8. A compound of claim 2, wherein $R_4$ represents hydrogen, morpholine or azepine.

9. A compound of claim 1 which is selected from:

2-(dipropylamino)-8-(4-thiomorpholinyl)pyrido[3,4-d]pyrimidin-4(3H)-one, 8-(1-azocanyl)-2-(dipropylamino)pyrido[3,4-d]pyrimidin-4(3H)-one, 8-((4aα,8aα)-octahydro-1(2H)-quinolyl)-2-(dipropylamino)pyrido[3,4-d]pyrimidin-4(3H)-one, 8-((4aβ,8aα)-octahydro-1(2H)-quinolyl)-2-(dipropylamino)pyrido[3,4-d]pyrimidin-4(3H)-one, 6,8-di(1-azepanyl)-2-(dipropylamino)pyrido[3,4-d]pyrimidin-4(3H)-one, 8-(1-azepanyl)-2-(dipropylamino)-6-(4-morpholinyl)pyrido[3,4-d]pyrimidin-4(3H)-one, 8-(1-azepanyl)-2,6-di(4-morpholinyl)pyrido[3,4-d]pyrimidin-4(3H)-one, 2-amino-8-[(3α,5β)-3,5-dimethylmorpholinyl]pyrido[3,4-d]pyrimidin-4(3H)-one, 2-amino-8-[(3α,5α)-3,5-dimethylmorpholinyl]pyrido[3,4-d]pyrimidin-4(3H)-one, 8-[(3α,5β)-3,5-dimethylmorpholinyl]-2-(dipropylamino)pyrido[3,4-d]pyrimidin-4(3H)-one, 8-[(3α,5α)-3,5-dimethylmorpholinyl]-2-(dipropylamino)pyrido[3,4-d]pyrimidin-4(3H)-one, 8-[(3α,5α)-3,5-dimethylmorpholinyl]-2-(4-morpholinyl)pyrido[3,4-d]pyrimidin-4(3H)-one, 2-amino-8-(1-azepanyl)-6-(4-morpholinyl)pyrido[3,4-d]pyrimidin-4(3H)-one, 8-chloro-2-(dipropylamino)pyrido[3,4-d]pyrimidin-4(3H)-one, 2-(dipropylamino)-8-(1-pyrrolidinyl)pyrido[3,4-d]pyrimidin-4(3H)-one, and 8-(3,4-dimethoxyphenyl)-2-(dipropylamino)pyrido[3,4-d]pyrimidin-4(3H)-one.

10. A method for treating a living animal body, including a human, afflicted with a hyperlipidaemia, comprising the step of administering to the living animal body an amount of a compound of claim 1 which is effective for alleviation of hyperllipidaemia.

11. The method of claim 10, wherein the living animal body is a human.

12. A pharmaceutical composition, comprising as active principle an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

| | |
|---|---|
| PATENT NO. | : 7,361,662 B2 |
| APPLICATION NO. | : 10/533697 |
| DATED | : April 22, 2008 |
| INVENTOR(S) | : Sylvain Rault et al. |

It is certified that error appears in the above-identified patent and that said Letters Patent is hereby corrected as shown below:

Column 10, Line 38/39:   Delete "including a human"

Signed and Sealed this

Twenty-first Day of April, 2009

JOHN DOLL
*Acting Director of the United States Patent and Trademark Office*